US008986276B2

(12) United States Patent
Kawakami et al.

(10) Patent No.: US 8,986,276 B2
(45) Date of Patent: Mar. 24, 2015

(54) DISPOSABLE WEARING ARTICLE

(75) Inventors: Yusuke Kawakami, Kanonji (JP);
Shoshi Kosaka, Kanonji (JP)

(73) Assignee: Unicharm Corporation, Ehime (JP)

( * ) Notice: Subject to any disclaimer, the term of this patent is extended or adjusted under 35 U.S.C. 154(b) by 198 days.

(21) Appl. No.: 13/643,655

(22) PCT Filed: May 17, 2011

(86) PCT No.: PCT/JP2011/061339
§ 371 (c)(1),
(2), (4) Date: Oct. 26, 2012

(87) PCT Pub. No.: WO2011/145627
PCT Pub. Date: Nov. 24, 2011

(65) Prior Publication Data
US 2013/0041340 A1    Feb. 14, 2013

(30) Foreign Application Priority Data
May 20, 2010 (JP) .................................. 2010-116775

(51) Int. Cl.
*A61F 13/15* (2006.01)
*A61F 13/49* (2006.01)
(Continued)

(52) U.S. Cl.
CPC ......... *A61F 13/496* (2013.01); *A61F 13/49001* (2013.01); *A61F 13/49009* (2013.01);
(Continued)

(58) Field of Classification Search
USPC ............... 604/385.28, 385.25, 385.26, 385.3, 604/385.24, 385.29
See application file for complete search history.

(56) References Cited

U.S. PATENT DOCUMENTS 5,749,865 A       5/1998   Yamamoto et al.
2005/0256492 A1 * 11/2005  Yamakawa et al. ...... 604/385.28
(Continued)

FOREIGN PATENT DOCUMENTS

| EP | 2087871 A1  | 8/2009  |
|----|-------------|---------|
| JP | 09038134 A  | 2/1997  |
| JP | 11504825 A  | 5/1999  |
| JP | 3515834 B2  | 4/2004  |
| JP | 2006346439 A| 12/2006 |
| JP | 2007029507 A| 2/2007  |
| JP | 200782890 A | 4/2007  |
| JP | 2009119078 A| 6/2009  |
| WO | 2009063666 A1| 5/2009 |

OTHER PUBLICATIONS

Supplementary European Search Report issued Mar. 28, 2014, corresponds to European patent application No. 11783561.1.
International Search Report and Written Opinion corresponding to PCT/JP2011/061339, dated Jul. 12, 2011.

*Primary Examiner* — Jacqueline F. Stephens
(74) *Attorney, Agent, or Firm* — Lowe Hauptman & Ham, LLP

(57) ABSTRACT

In a disposable wearing article, front and rear waist elastics are attached between respective outer and inner sheets. An absorbent structure and leg-cuffs are attached to an inner side of the inner sheet. Lateral proximal portions of the respective leg cuffs are bonded between the absorbent structure and the inner sheet and lateral distal portions of the respective leg cuffs extend outwardly in a transverse direction beyond the absorbent structure and are not bonded to the inner sheet. These lateral distal portions are provided with a plurality of cuff elastics. Front and rear waist regions respectively include first through third sub-regions which are adjacent one to another in this order and the respective sub-regions are provided with first through third waist elastics. A tensile stress in the first and third sub-regions is higher than that in the second sub-region and the cuff elastics extend to at least the second sub-region.

6 Claims, 4 Drawing Sheets

(51) Int. Cl.
*A61F 13/494* (2006.01)
*A61F 13/496* (2006.01)

(52) U.S. Cl.
CPC ..... *A61F13/49011* (2013.01); *A61F 13/49017* (2013.01); *A61F 13/49019* (2013.01); *A61F 13/49061* (2013.01); *A61F 13/49406* (2013.01); *A61F 13/4946* (2013.01); *A61F 2013/15292* (2013.01); *A61F 2013/15357* (2013.01); *A61F 2013/49493* (2013.01)

USPC ............ 604/385.28; 604/385.25; 604/385.26; 604/385.3; 604/385.24; 604/385.29

(56) References Cited

U.S. PATENT DOCUMENTS

| | | |
|---|---|---|
| 2006/0264859 A1 | 11/2006 | Tsuji et al. |
| 2010/0312214 A1 | 12/2010 | Shimada et al. |
| 2011/0022019 A1 | 1/2011 | Shimada et al. |

\* cited by examiner

DISPOSABLE WEARING ARTICLE

TECHNICAL FIELD

The present invention relates to disposable wearing articles and more specifically to disposable wearing articles, for example, disposable diapers, toilet-training pants or incontinence briefs, each including a plurality of elastics attached to waist regions.

BACKGROUND

Conventionally, disposable diapers including front and rear waist regions, a crotch region extending between these waist regions and an absorbent structure attached to at least the crotch region are known. For example, JP H11-504825 A (PTL 1) discloses a disposable diaper including elastic elements contractibly attached under tension to the diaper along first to fourth routes so that an absorbent structure may be surrounded by these routes and a crotch region may billow in a bowl-shape toward the wearer's garment. Specifically, the first and second routes extend from one lateral edge of the front waist region across a longitudinal center line of the diaper to one lateral edge of the rear waist region diagonally opposite to the one lateral edge of the front waist region. The third and fourth routes extend in a mirror symmetric relation about the longitudinal center line.

Upon contraction of the elastic elements attached along the first to fourth routes, the area surrounded by these elastic elements billows in a bowl-shape and bodily fluids, for example, urine may be temporarily collected so as to be reliably absorbed by the absorbent structure and thereby to prevent bodily fluids such as urine from leaking out of the diaper.

CITATION LIST

Patent Literature

{PTL 1}: JP H11-504825 A

SUMMARY

Technical Problem

In the diaper disclosed in PTL 1, the elastic elements arranged along the first to fourth routes define totally four points of intersections. At these points of intersection of the elastic elements, a tightening force exerted on the diaper wearer is more notable than that along the remaining segments and locally put in tight contact with the wearer's body, as a result, the wearer might experience notably uncomfortable irritation.

An object of this invention is to provide a disposable wearing article having a cup-shaped portion adapted for temporary collection of bodily fluids such as urine without irritating the wearer's skin.

Solution to Problem

Some embodiments of the present invention provide a disposable wearing article having a longitudinal direction and a transverse direction. The disposable wearing article includes: a skin-facing side; a non-skin-facing side; a chassis including a front waist region, a rear waist region and a crotch region extending between the front and rear waist regions; a waist-opening defined by front and rear ends of the chassis; a pair of leg-openings defined by opposite lateral edges of the chassis, an absorbent structure lying at least in the crotch region; and a pair of leg-cuffs lying on the skin-facing side of the chassis, extending across the crotch region into the front and rear waist regions and spaced apart from each other in the transverse direction. A plurality of front and rear waist elastics arranged to extend in the transverse direction and to be spaced apart from each other in the longitudinal direction are contractibly attached under tension to the front and rear waist regions.

This invention further includes the following features:

the chassis includes an inner sheet lying on the skin-facing side, an outer sheet lying on the non-skin-facing side, and the waist elastics attached between the inner and outer sheets;

the absorbent structure extends across the crotch region into the front and rear waist regions;

the leg-cuffs respectively include lateral proximal portions bonded to the chassis, lateral distal portions opposed to the lateral proximal portions and adapted to be spaced upward from the chassis, and cuff elastics contractibly attached under tension to the lateral distal portions;

at least one of the front and rear waist elastics include first waist elastics lying on the chassis outboard of the absorbent structure as viewed in the longitudinal direction and third waist elastics attached so as to extend along at least portions of the leg-opening; and at least one of the front and rear waist regions includes a first sub-region provided with the first waist elastics, a third sub-region provided with the third waist elastics, and a second sub-region lying between the first and third sub-regions, wherein a tensile stress in the first and third sub-regions is higher than that in the second sub-region and the cuff elastics extend at least to the second sub-region.

According to an embodiment of this invention, the front and rear waist elastics include the second waist elastics attached to the second sub-region.

According to another embodiment of this invention, the respective lateral distal portions in the leg-cuffs are bonded to the side of the chassis in regions overlapping the first sub-region.

According to even another embodiment of this invention, a tensile stress in the first sub-region and the third sub-region is in a range of 0.5 to 3.0 N and a tensile stress in the second sub-region is in a range of 0.1 to 1.5 N.

According to still another embodiment of this invention, a stiffness value in the first through third sub-regions inclusive of the absorbent structure is in a range of 0.05 to 1.00 N*cm.

According to yet another embodiment of this invention, the absorbent structure includes a liquid-absorbent core and is formed at least in regions overlapping the third sub-region with core material lessened areas in which the amount of core material is less than in a remaining area.

Advantageous Effects of Invention

According to one or more embodiments of this invention, the tensile stress in the second sub-region, in at least one of the front and rear waist regions, is lower than those in the first and third sub-region so that the opposite lateral edges of this second sub-region may be contracted under the effect of the cuff elastics to form the cup-shaped area swollen outward. The waist elastics are attached between the inner and outer sheets and the cuff elastics are attached to the skin-facing side of the inner sheet. In consequence, these elastics should not overlap and come in direct contact with each other and therefore it is possible to prevent an excessive tightening force from locally developing.

DESCRIPTION OF EMBODIMENTS

Figure 1:
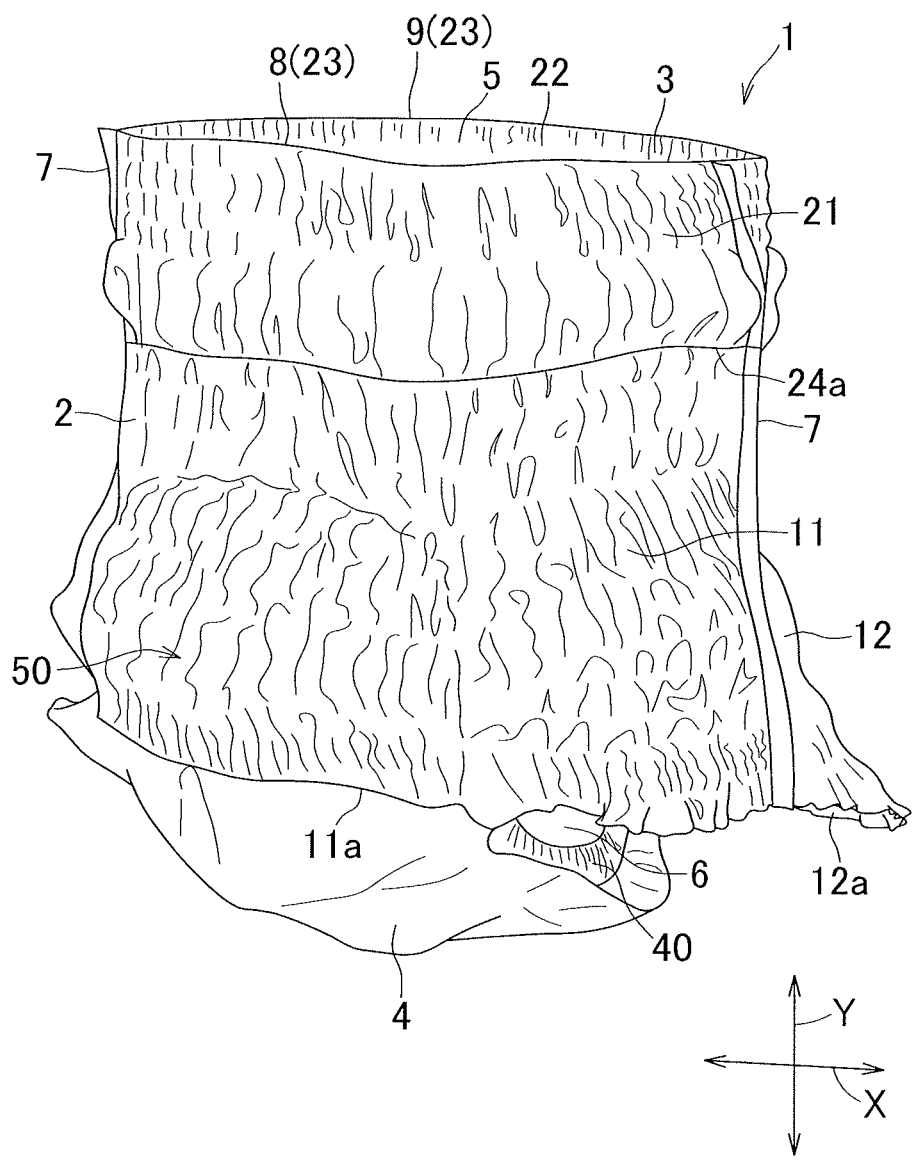
FIG. 1 is a perspective view of a disposable diaper as an example of the disposable wearing article.
Figure 2:
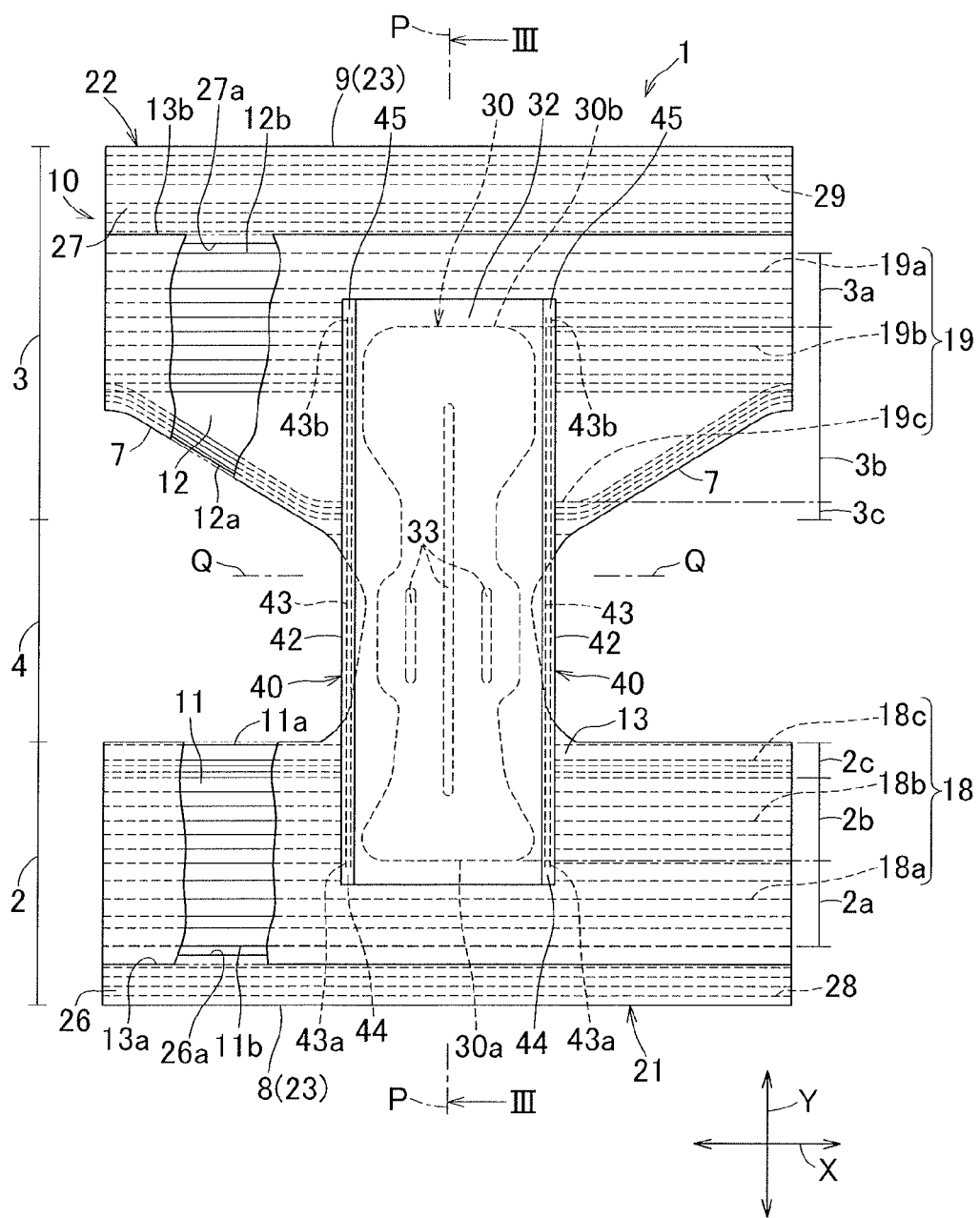
FIG. 2 is a developed plan view of the diaper.
Figure 3:
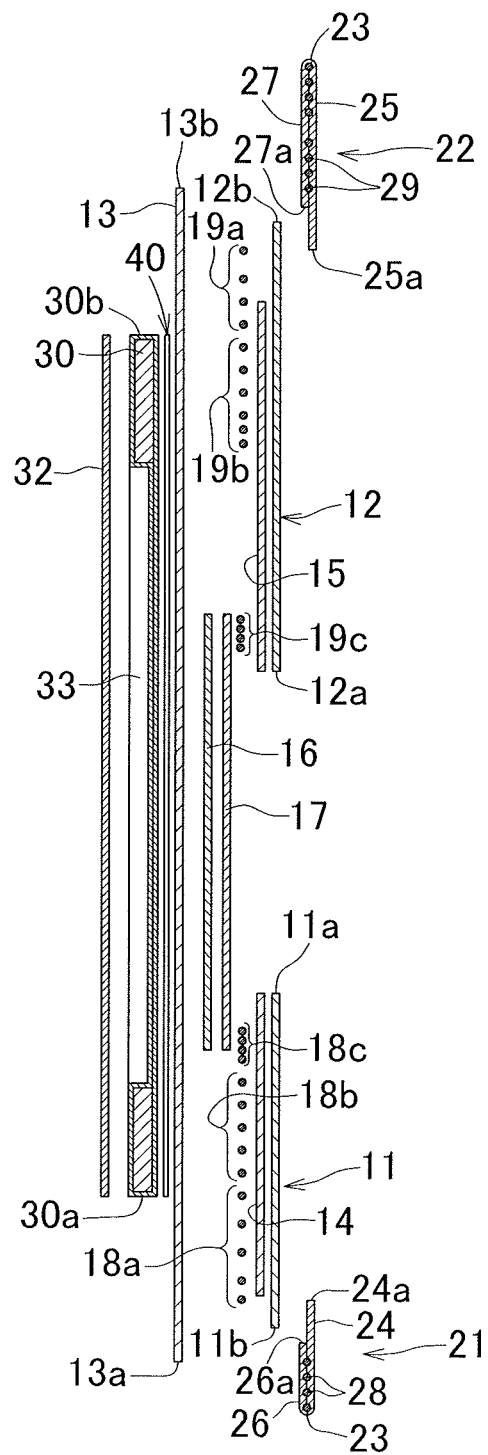
FIG. 3 is a schematic sectional view taken along line III-III in FIG. 2.
Figure 4:
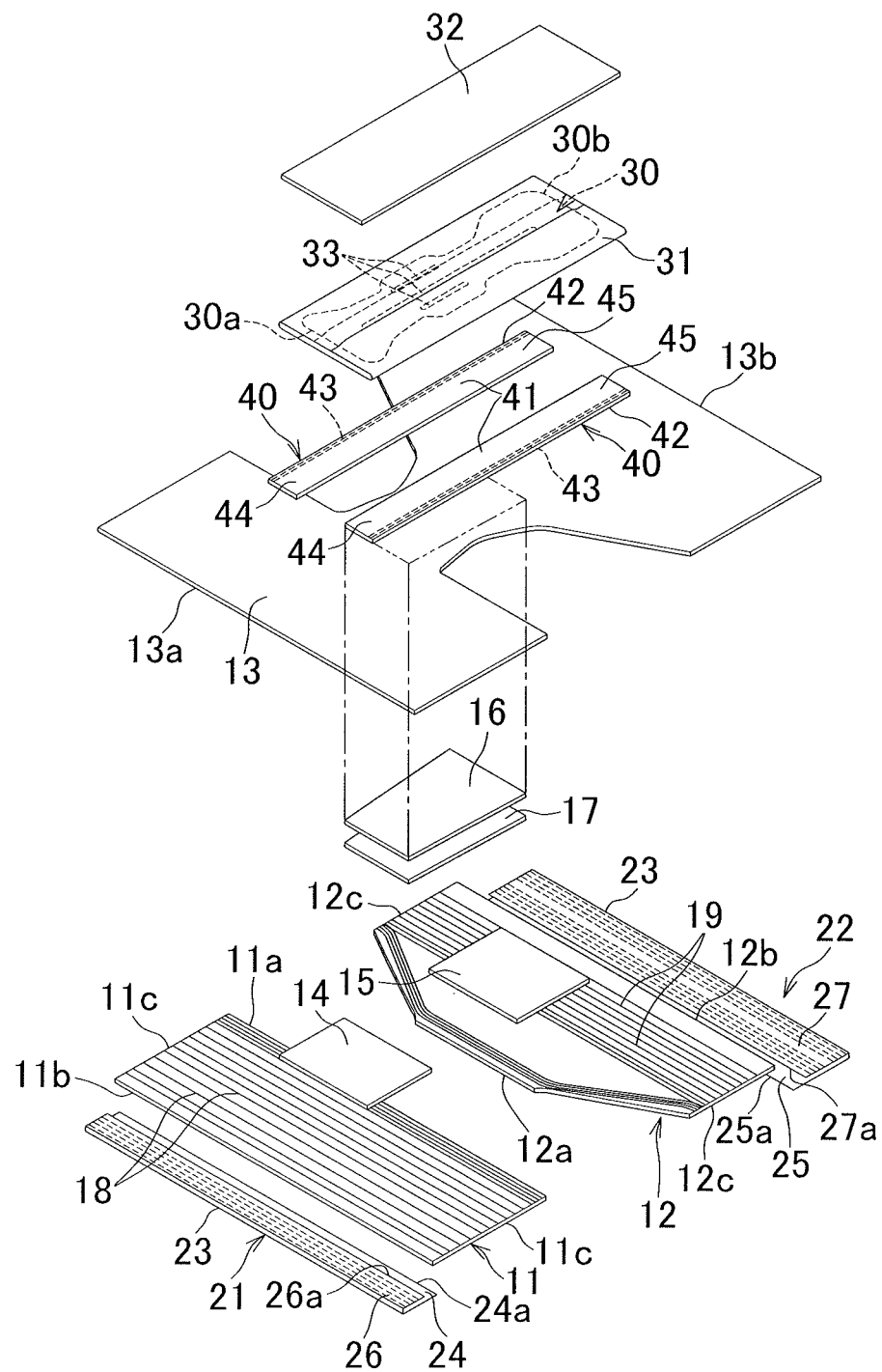
FIG. 4 is an exploded perspective view corresponding to FIG. 2.

FIGS. 1 through 4 illustrate an embodiment of this invention and a disposable diaper will be described hereunder as an example of the disposable wearing articles according to this invention with reference to FIGS. 1 through 4. FIG. 1 is a perspective view illustrating the diaper 1 with a waist-opening 5 as well as leg-openings 6 being kept in annular states, respectively and FIG. 2 is a developed plan view of the diaper 1 as viewed from the skin-facing side wherein the diaper 1 is kept flat with respective elastics of the diaper being stretched against the contractile force thereof. FIG. 3 is a sectional view taken along line III-III in FIG. 2, schematically illustrating the diaper 1 with respective constituent sheets being spaced apart from each other. FIG. 4 is an exploded perspective view corresponding to FIG. 2.

The diaper 1 has a longitudinal direction Y and a transverse direction X and includes a skin-facing side, a non-skin-facing side, i.e., a garment-facing side, a front waist region 2, a rear waist region 3, a crotch region 4 extending between the front and rear waist regions 2, 3. The front and rear waist regions 2, 3 are bonded to each other along respective pairs of opposite lateral edges 7 thereof and thereupon front and rear ends 8, 9 of the diaper 1 extending in the transverse direction X cooperate with each other to form the waist-opening 5 and segments of the opposite lateral edges 7 extending in the crotch region 4 cooperate with each other to form the leg-openings 6. The diaper 1 has, in addition, longitudinally extending imaginary center line P-P bisecting a dimension in the longitudinal direction Y of the diaper 1 and transversely extending imaginary center line Q-Q bisecting a dimension of the diaper 1 in the longitudinal direction Y wherein the diaper 1 is formed so as to be substantially symmetric about the longitudinally extending imaginary center line P-P. The opposite lateral edges 7 are curved toward the longitudinally extending imaginary center line P-P in the crotch region 4 so that a dimension of the crotch region 4 in the transverse direction X may be gradually reduced.

The diaper 1 includes a chassis 10 having the front and rear waist regions and the crotch region 4, an absorbent structure 30 lying on the skin-facing side of the chassis 10 and extending across the crotch region 4 into the front and rear waist regions 2, 3, and a pair of leg-cuffs 40.

The chassis 10 includes front and rear outer sheets 11, 12 lying on the garment-facing side and partially defining the front and rear waist regions 2, 3, an inner sheet 13 lying on the inner side of the front and rear outer sheets 11, 12 and partially overlapping these outer sheets 11, 12 so as to define the crotch region 4 and respective parts of the front and rear waist regions 2, 3. The front and rear outer sheets 11, 12 are spaced apart from each other in the longitudinal direction Y and the inner sheet 13 is located so as to connect these two sheets 11, 12 to each other. As material of the front and rear outer sheets 11, 12 and the inner sheet 13, for example, a hydrophobic spunbonded fibrous nonwoven fabric or an SMS (spunbonded-meltblown-spunbonded) fibrous nonwoven fabric may be used.

The front outer sheet 11 includes inner and outer ends 11a, 11b extending in the transverse direction X and opposite lateral edges 11c extending in the longitudinal direction Y to define a substantially rectangular shape as a whole. The rear outer sheet 12 has inner and outer ends 12a, 12b extending in the transverse direction X and opposite lateral edges 12c extending in the longitudinal direction Y, wherein the front and rear outer sheets 11, 12 are in such a dimensional relationship that, when the respective outer ends 11b, 12b of the front and rear outer sheets 11, 12 are overlapped with each other, the inner end 12a of the rear outer sheet 12 extends outward beyond the inner end 11a of the front outer sheet 11. This protruding region has a substantially trapezoidal shape.

Between the front and rear outer sheets 11, 12 and the inner sheet 13, there are provided a front leakage-barrier sheet 14 bonded to the front outer sheet 11, a rear leakage-barrier sheet 15 bonded to the rear outer sheet 12 and a crotch leakage-barrier sheet 16 located between these front and rear leakage-barrier sheets 14, 15 as viewed in the longitudinal direction Y and bonded to inner sheet 13, wherein a cover sheet 17 is bonded to the garment-facing side of the crotch leakage-barrier sheet 16. As material of these leakage-barrier sheets 14, 15, 16, for example, a hydrophobic and breathable plastic film may be used and thereby leakage of bodily fluids such as urine out of the diaper 1 may be prevented. The crotch leakage-barrier sheet 16 and the cover sheet 17 are substantially the same in shape as well as in size wherein, as material of the cover sheet 17, for example, a hydrophobic fibrous nonwoven fabric may be used. The respective outer surfaces of the front and rear leakage-barrier sheets 14, 15 may be covered with the front and rear outer sheets 11, 12, respectively, and the outer surface of the crotch leakage-barrier sheet 16 may be covered with the cover sheet 17 to improve the texture of the diaper 1 on the garment-facing side. As means for bonding the respective sheets to each other, for example, hot melt adhesives may be used.

A plurality of front waist elastics 18 are contractibly attached under tension in the transverse direction between the front outer sheet 11 and the inner sheet 13. In a similar fashion, rear waist elastics 19 are attached between the rear outer sheet 12 and the inner sheet 13. These front and rear waist elastics 18, 19 are arranged to be spaced apart from each other in the longitudinal direction Y and bonded to at least one of the front and rear outer sheets 11, 12 and the inner sheet 13 by suitable bonding means such as hot melt adhesives.

Front and rear waist-opening sheets 21, 22 are joined to the outer ends of the front and rear outer sheets 11, 12 as viewed in the longitudinal direction Y, respectively. More specifically, the front waist-opening sheet 21 is bonded to the outer end 11b of the front outer sheet 11 and the rear waist-opening sheet 22 is bonded to the outer end 12b of the rear outer sheet 12. The front and rear waist-opening sheets 21, 22 are respectively divided along respective boundaries 23 into first sheet segments 24, 25 lying on the outer surface side and second sheet segments 26, 27 lying on the inner surface side. More specifically, the front and rear front and rear waist-opening sheets 21, 22 are folded along the respective boundaries 23 and the first sheet segments 24, 25 and the second sheet segments 26, 27 are laminated to each other, respectively. The boundaries 23 define the waist-opening 5 and, at the same time, define the front and rear ends 8, 9 of the chassis 10 (See FIG. 1). A plurality of front and rear waist-opening sheets elastics 28, 29 are contractibly attached under tension between the first sheet segments 24, 25 and the second sheet segments 26, 27, respectively. The front and rear front and rear waist-opening sheets elastics 28, 29 are respectively spaced apart from each other in the longitudinal direction Y and bonded to at least one of the first sheet segments 24, 25 and the second sheet segments 26, 27 by bonding means such as hot melt adhesives.

According to this embodiment, a range extending from the boundary 23 of the front waist-opening sheet 21 to the inner end 11*a* of the front outer sheet 11 is defined as the front waist region 2 and a range extending from the boundary 23 of the rear waist-opening sheet 22 to the inner end 12*a* of the rear outer sheet 12 is defined as the rear waist region 3. A region extending between the inner end 11*a* and the inner end 12*a* is defined as the crotch region 4.

An absorbent structure 30 is attached to the inner surface side of the inner sheet 13. The absorbent structure 30 includes the core including fluff pulp or superabsorbent polymer particles or a mixture thereof and is wrapped with a liquid-pervious sheet 31 such as tissue paper. A body side liner 32 is attached to the absorption surface of the absorbent structure 30. As material of the body side liner 32, a liquid-pervious fibrous nonwoven fabric, for example, an air-through nonwoven fabric or a spunbonded nonwoven fabric may be used. The absorbent structure 30 is formed with core material lessened areas 33 extending in the longitudinal direction Y and a core material content therein lessened in comparison with the area surrounding these core material lessened areas 33. Specifically, the core material lessened areas 33 are provided in the form of a plurality of slits in which the core material is locally removed. In consequence, substantially no core material is present in these core material lessened areas 33 and the absorbent structure 30 may be easily folded along these core material lessened areas 33 and easily put in close contact with the wearer's body. Further, formation of the core material lessened areas 33 makes it possible to enlarge the absorptive surface area of the core and thereby to accelerate the absorption of bodily fluids such as urine.

A pair of leg-cuffs 40 is disposed between the absorbent structure 30 and the inner sheet 13. The leg-cuffs 40 are arranged to be spaced apart from each other in the transverse direction X and to extend in the longitudinal direction Y. Each of the leg-cuffs 40 has a lateral proximal portion 41 extending in the inner side and a lateral distal portion 42 extending in the outer side respectively as viewed in the transverse direction X. The lateral proximal portion 41 is bonded between the absorbent structure 30 and the inner sheet 13 by bonding means such as hot melt adhesives. The lateral distal portion 42 extends outward in the transverse direction X beyond the absorbent structure 30 and extends in the longitudinal direction Y without being bonded to the inner sheet 13 wherein the lateral distal portion 42 is provided with a plurality of cuff elastics 43 contractibly attached thereto under tension in the longitudinal direction Y. Front and rear end portions 44, 45 of the leg-cuff 40 are bonded to the inner sheet 13 by suitable bonding means such as hot melt adhesives. In these leg-cuffs 40, upon contraction of the cuff elastics 43, the lateral distal portions 42 are spaced away upward from the inner sheet 13 and come in close contact with the vicinities of the wearer's thighs, thereby containing bodily fluids such as urine within the diaper 1.

In the diaper 1 as has been described above, the front waist elastics 18 include:

a plurality of first waist elastics 18*a* lying outboard of a front end 30*a* of the absorbent structure 30 as viewed in the longitudinal direction Y;

a plurality of second waist elastics 18*b* lying outboard of the first waist elastics 18*a* as viewed in the longitudinal direction Y so that at least middle segments thereof as viewed in the transverse direction X may overlap the absorbent structure 30; and a plurality of third waist elastics 18*c* lying inside the second waist elastics 18*b* as viewed in the longitudinal direction Y so that at least middle segments thereof as viewed in the transverse direction X may overlap the absorbent structure 30. Specifically, the first waist elastics 18*a* are arranged to extend between the outer end 11*b* of the front waist's outer sheet 11 and the front end 30*a* of the absorbent structure 30, the third waist elastics 18*c* are arranged to extend along the inner end 11*a* and the second waist elastics 18*b* are arranged to extend between these first and third waist elastics 18*a*, 18*c*. In the front waist region 2, a first sub-region 2*a* provided with the first waist elastics 18*a*, a second sub-region 2*b* provided with the second waist elastics 18*b* and a third sub-region 2*c* provided with the third waist elastics 18*c* are defined so that these sub-regions may be adjacent in this order. Respective portions of the core material lessened regions 33 extending from the crotch region 4 overlap at least the third sub-region 2*c*.

In this embodiment, a dimension in the longitudinal direction Y of the first sub-region 2*a* is set to about 65 mm. A tensile stress of this first sub-region 2*a* may be in a range of about 0.5 to about 3.0 N and, in this embodiment, this tensile stress is set to about 0.95 N. The first waist elastics 18*a* include five elastic yarns/threads having a fineness of about 620 dtex and are attached at a stretching ratio in a range of about 1.8 to about 2.5 and at a pitch in a range of about 10 to about 15 mm. A dimension in the longitudinal direction Y of the second sub-region 2*b* is set to about 60 mm. A tensile stress of this second sub-region 2*b* may be in a range of about 0.1 to about 1.5 N and, in this embodiment, this tensile stress is set to about 0.63 N. The second waist elastics 18*b* include five elastic yarns/threads having a fineness of about 620 dtex and are attached at a stretching ratio of about 1.8 and a pitch of about 12 mm. A dimension in the longitudinal direction Y of the third sub-region 2*c* is set to about 25 mm. A tensile stress of this third sub-region 2*c* may be in a range of about 0.5 to about 3.0 N and, in this embodiment, this tensile stress is set to about 0.67 N. The third waist elastics 18*c* include four elastic yarns/threads having a fineness of about 620 dtex and are attached at a stretching ratio of about 1.8 and at a pitch of about 5 mm.

The tensile stress was measured by a method as will be described below.

After the absorbent structure 30 had been peeled off from the chassis 10 of the diaper 1, the respective sub-regions were cut off in predetermined sizes to be used as test pieces. More specifically, a piece having a dimension of 150 mm in the transverse direction X and a dimension of 65 mm in the longitudinal direction Y was cut from the first sub-region 2*a*, a piece having a dimension of 150 mm in the transverse direction X and a dimension of 60 mm in the longitudinal direction Y was cut from the second sub-region 2*b* and a piece having a dimension of 150 mm in the transverse direction X and a dimension of 25 mm in the longitudinal direction Y was cut from the third sub-region 2*c* as respective test pieces for these sub-regions. After the respective test pieces had been left at rest for 24 hours at constant temperature and humidity, specifically, at a temperature in a range of about 20 to 23° C. and a humidity in a range of about 60 to about 65% RH with the elastics left in a relaxed condition, the tensile stress values thereof were measured with use of Tensile Tester (manufactured by Instron Japan Co., Ltd.).

The respective test pieces were provided with markings indicating a predetermined dimension (A mm) in the transverse direction X and held by chucks at the positions corresponding to the respective markings. In a cycle mode of 2 cycles and at a stretching rate of 100 mm/min, each of the test pieces was stretched by 90% (B mm) of the initial dimension of the test piece, i.e., an initial distance between the markings (A mm). Having reached the point corresponding to the inter-chuck distance of B mm (B-point), the chuck was reversed and the second cycle was started. A load at the B-point in the second cycle was measured and 85% of this load was recorded as the tensile stress. A plurality of such measurements were carried out for the respective test pieces and average values were recorded as the tensile stress values of the respective test pieces in this embodiment.

Stiffness value in the longitudinal direction Y of the first through third sub-regions $2a$ through $2c$ may be in a range of about 0.08 to 1.00 N*cm and is about 0.13 N*cm in this embodiment. Stiffness value in the transverse direction X of the first and second sub-regions $2a$, $2b$ may be in a range of about 0.08 to about 1.00 N*cm and is about 0.11N*cm in this embodiment. Stiffness value of the third sub-region $2c$ in the transverse direction X may be in a range of about 0.05 to about 1.00 N*cm and is about 0.07 N*cm in this embodiment.

The stiffness value was measured with use of a method as will be described below.

The stiffness value was measured with use of Taber Stiffness Tester (manufactured by Yasuda Seiki Seisakusho LTD. in Japan). A test piece including both the chassis 10 and the absorbent structure 30 having a dimension of about 70 mm in the longitudinal direction Y and a dimension of about 38.1 mm in the transverse direction X was cut off from the diaper. After a dimension (C) of the test piece in the thickness direction had been measured, this test piece was gently pinched by chucks so that the test piece may be merely kept in contact with centers of the chucks. A clearance between a support roller and the test piece was adjusted to be equal to the dimension (C)×0.08 (mm) and then an auxiliary weight was overlaid thereon. The test piece was rotated together with the roller in right and left directions and a graduation (D) on the right side and a graduation (E) on left side were read off at a moment when respective scores indicating 15° were aligned with a central score of a pendulum, respectively. Stiffness value was obtained from a formula: (D)+(E)/2×(numerical value of the auxiliary weight)/1000×9.807. The measurement was carried out more than once and an average of measured values was recorded as the stiffness value in this embodiment.

The rear waist elastics 19 include:

a plurality of first waist elastics $19a$ lying outboard of a rear end $30b$ of the absorbent structure 30 as viewed in the longitudinal direction Y;

a plurality of second waist elastics $19b$ lying inside the first waist elastics $19a$ as viewed in the longitudinal direction Y so that at least middle segments thereof as viewed in the transverse direction X may overlap the absorbent structure 30; and a plurality of third waist elastics $19c$ lying inside the second waist elastics $19b$ as viewed in the longitudinal direction Y so that at least middle segments thereof as viewed in the transverse direction X may overlap the absorbent structure 30. Specifically, the first waist elastics $19a$ are arranged to extend between the outer end $12b$ of the rear waist's outer sheet 12 and the rear end $30b$ of the absorbent structure 30, the third waist elastics $19c$ are arranged so as to extend along the inner end $11a$ and the second waist elastics $19b$ are arranged to extend between these first and third waist elastics $19a$, $19c$. In the rear waist region 3, a first sub-region $3a$ provided with the first waist elastics $19a$, a second sub-region $3b$ provided with the second waist elastics $19b$ and a third sub-region $3c$ provided with the third waist elastics $19c$ are defined so that these sub-regions may be adjacent in this order. The third sub-region $3c$ includes at least an area in which the third waist elastics $19c$ overlap the absorbent structure 30. Respective portions of the core material lessened regions 33 extending from the crotch region 4 partially overlap the third sub-region $3c$.

In this embodiment, a dimension in the longitudinal direction Y of the first sub-region $3a$ is set to be about 50 mm. A stretching ratio in this first sub-region $3a$ may be in a range of about 0.5 to 3.0 N and this tensile stress in this embodiment is set to about 0.74 N. The first waist elastics $19a$ include four elastic yarns/threads having a fineness of about 620 dtex and are attached at a stretching ratio in a range of about 1.8 to about 2.5 and at a pitch in a range of about 12 to about 15 mm. A dimension in the longitudinal direction Y of the second sub-region $3b$ is set to about 145 mm. A tensile stress of this second sub-region $3b$ may be in a range of about 0.1 to 1.5 N and, in this embodiment, this tensile stress is set to about 0.67 N. The second waist elastics $19b$ include six elastic yarns/threads having a fineness of about 620 dtex and are attached at a stretching ratio in a range of about 1.4 to about 1.8 and a pitch in a range of about 7 to about 12 mm. A dimension in the longitudinal direction Y of the third sub-region $3c$ is set to about 25 mm. A tensile stress of this third sub-region $3c$ may be in a range of about 0.5 to about 1.5 N and, in this embodiment, this tensile stress is set to about 0.53 N. The third elastics $19c$ include four elastic yarns/threads having a fineness of about 620 dtex and are attached at a stretching ratio of about 1.4 and at a pitch of about 5 mm. The tensile stress was measured with the same method for the front waist region 2. In this regard, in the second sub-region $3b$, the second waist elastics $19b$ were attached so as to be biased toward the first sub-region $3a$ and the tensile stress was measured in the area provided with the elastics.

Stiffness value in the longitudinal direction Y of the first through third sub-regions $3a$ through $3c$ may be in a range of about 0.08 to 1.00 N*cm and, in this embodiment, this stiffness value is about 0.13 N*cm. Stiffness value in the transverse direction X of the first and second sub-regions $3a$, $3b$ may be in a range of about 0.08 to about 1.00 N*cm and, in this embodiment, this stiffness value is about 0.11 N*cm. Stiffness value of the third sub-region $3c$ in the transverse direction X may be in a range of about 0.05 to about 1.00 N*cm and, in this embodiment, this stiffness value is about 0.07 N*cm. The stiffness value was measured with use of the same method as for the front waist region 2.

The cuff elastics 43 attached to the respective lateral distal portions 42, 42 extend from the crotch region 4 into the front and rear waist regions 2, 3 and respective front and rear end portions $43a$, $43b$ extend beyond the second and third sub-regions $2b$, $2c$, $3b$, $3c$ of the front and rear waist regions 2, 3 to the first sub-regions $2b$, $3b$. Namely, the front and rear end portions $43a$, $43b$ lie outboard of the front and rear ends $30a$, $30b$ of the absorbent structure 30 as viewed in the longitudinal direction Y. The front and rear end portions 44, 45 of the respective lateral distal portions 42 are bonded to the inner sheet 13 and thereby the front and rear end portions $43a$, $43b$ of the cuff elastics 43 also are bonded to the inner sheet 13. The cuff elastics 43 indirectly overlap with the front and rear waist elastics 18, 19 by the intermediary of the inner sheet 13, in other words, without being put in direct contact with each other. As the cuff elastics 43, two elastic yarns/threads having a fineness of about 620 dtex are used and attached at a stretching ratio of about 2.5 and at a pitch of about 5 mm.

In the aforementioned diaper 1, the tensile stress in the first and third sub-regions 2a, 2c of the front waist region 2 is higher than that in the second sub-region 2b and, in the similar manner, the tensile stress in the first and third sub-regions 3a, 3c of the rear waist region 3 is higher than that in the second sub-region 3b. Therefore, in the first and third sub-regions 2a, 2c; 3a, 3c of the front and rear waist regions 2, 3 extending outboard of the respective second sub-regions 2b, 3b of the front and rear waist regions 2, 3 as viewed in the longitudinal direction Y, the diaper 1 is more closely tightened around the wearer's body under contraction of the first and third waist elastics 18a, 18c; 19a, 19c. In addition, the contractile force of the cuff elastics 43 is exerted on the first through third sub-regions 2a through 2c; 3a through 3c. Thus, the second sub-regions 2b, 3b are peripherally contracted by the respective elastics and, in consequence, in the front and rear waist regions 2, 3, cup-shaped areas 50 protruding outward are formed in the second sub-regions 2b, 3b (See FIG. 1) particularly in the diaper 1 put on the wearer's body.

The cup-shaped areas 50 formed in the front and rear waist regions 2, 3 in this manner may temporarily retain body waste and the absorbent structure 30 lying in the cup-shaped areas 50 may reliably absorb a liquid content in such body waste to prevent such liquid content from leaking out of the diaper 1. Particularly when body waste containing a large amount of liquid is excreted, it is difficult for the absorbent structure 30 to absorb such liquid content at once and such liquid content might leak out of the diaper 1. However, according to this invention, formation of the cup-shaped areas 50 ensures that such leakage may be prevented. Additionally, formation of the cup-shaped areas 50 ensures that the inner sheet 13 in the second sub-regions 2b, 3b is spaced apart from the wearer's body to improve a ventilation within the diaper 1 and thereby to prevent stuffiness from being generated within the diaper 1 and to protect the wearer against suffering from diaper rash.

The cuff elastics 43 and the front and rear waist elastics 18, 19 do not directly intersect with each other and, as a result, a tightening force should not be locally intensified in direct intersections of these elasticizing members and these intersections should not come in excessively close contact with the wearer's body. In this diaper 1, consequently, it is possible to prevent the regions provided with the elastics from locally come in excessively tight contact with the wearer's body and irritate the wearer's skin.

The absorbent structure 30 is formed with the core material lessened areas 33 along which the absorbent structure 30 may be easily folded and further facilitate the cup-shaped areas 50 to be formed. In addition, these core material lessened areas 33 make it possible to enlarge the absorbent area and thereby to absorb body waste correspondingly at a higher rate. Further, the core material lessened areas make it possible to reduce the stiffness in the transverse direction X of the third sub-regions 2c, 3c and thereby to facilitate these third sub-regions 2c, 3c to be contracted under the effect of the third waist elastics 18c, 19c. The presence of the core material lessened areas 33 ensures the lower ends of the respective cup-like areas to be defined and thereby to put these lower ends in close contact with the wearer's body. Consequently, it is possible to restrict leakage of body waste, for example, urine beyond the lower ends of the respective cup-shaped areas 50 and thereby to ensure body waste such as urine to be retained in these cup-shaped areas 50.

While the stiffness values in the region of the diaper 1 in which the absorbent structure 30 overlaps the chassis have been described above to be in a range of about 0.08 to about 1.00 N*cm in the longitudinal direction Y and to be in a range of about 0.05 to about 1.00 N*cm in the transverse direction X, it is possible to set the stiffness value both in the longitudinal direction Y and in the transverse direction X to in a range of about 0.05 to 1.00 N*cm and it is also possible to set the stiffness values in both the longitudinal direction Y and the transverse direction X to one and same value. In this embodiment, the absorbent structure 30 is formed with the core material lessened areas 33 and, as a result, the stiffness value in the transverse direction X is lower than that in the longitudinal direction Y. If the stiffness value is lower than 0.05 N*cm, the cup-shaped areas 50 once having been formed will be collapsed under the contractile force of the front and rear waist elastics 18, 19. If the stiffness value is higher than 1.00 N*cm, the first and third sub-regions may not be contracted and it will be difficult to form the cup-shaped areas 50.

The third waist elastics 18c, 19c are attached along the inner ends 11a, 12a of the front and rear outer sheets 11, 12. These inner ends 11a, 12a partially define the leg-openings 6 and serve to put the leg-openings 6 in close contact around the wearer's legs to prevent body waste from leaking out beyond the peripheries of the respective leg-openings 6.

The cup-shaped area 50 may be formed in one of the front and rear waist regions 2, 3. The second sub-regions 2b, 3b may be provided with none of the elastics as the case may be. This is because the tensile stress in the second sub-regions 2b, 3b lower than those in the first and third sub-regions 2a, 2c; 3a, 3c facilitates the cup-shaped areas 50. Therefore, the second sub-regions 2b, 3b may include none of the elastics so long as the case is applicable to the aforementioned condition. In this regard, depending on the manner in which the diaper 1 is put on the wearer's body, the elastics may be attached to the second sub-regions 2b, 3b to keep these second sub-regions 2b, 3b in contact with the wearer's skin and thereby to absorb body waste such as urine by these second sub-regions 2b, 3b. While the tensile stress values in the first and third sub-regions are substantially equal to each other in this embodiment, it is essential that the tensile stress values of the first and third sub-regions are lower than that of the second sub-region.

The dimensions in the longitudinal direction Y of the first through third sub-regions are not limited to those having been described on the basis of this embodiment. In addition to these dimensions, the number of the respective elastics, the pitches at which these elastics are arranged, the fineness values and the other factors are also not limited to them having been described on the basis of this embodiment and may be appropriately varied so long as the cup-shaped areas may be reliably formed.

While the front and rear waist-opening defining sheets 21, 22 are additionally attached in this embodiment, the chassis 10 may be defined by the front and rear 11, 12 and the inner-sheet 13 without additionally attaching the front and rear waist-opening defining sheets 21, 22. While the front and rear outer sheets 11, 12 are spaced apart from each other in the longitudinal direction Y in this embodiment, it is not essential for the outer sheet to include two separate sheets spaced apart from each other but it is possible to use a single continuous outer sheet for the front and rear waist regions. This invention has been described above on the basis of the embodiment in the form of a pull-on pants-type diaper having the front and rear waist regions previously bonded to each other along the respective opposite lateral edges, this invention is applicable also to open-type diaper having the front and rear waist regions not previously bonded to each other along the respective opposite lateral edges.

The constituent members of the diaper 1 are not limited to those described in the specification but the other types of material widely used in the relevant technical field may be used without limitation.

The terms "first", "second" and "third" used in the description and claims of this invention are used merely to distinguish the similar elements, the similar positions or the other similar means.

REFERENCE SIGNS LIST 1 diaper (disposable wearing article)
2 front waist region
3 rear waist region
4 crotch region
5 waist-opening
6 leg-openings
7 opposite lateral edges
8 front end
9 rear end
10 chassis
11 front outer sheet (outer sheet)
12 rear outer sheet (outer sheet)
13 inner sheet
18 front waist elastics
18a first waist elastics
18b second waist elastics
18c third waist elastics
19 rear waist elastics
19a first waist elastics
19b second waist elastics
19c third waist elastics
30 absorbent structure
33 core material lessened regions
40 leg-cuffs
41 lateral proximal portions
42 lateral distal portions
43 cuff elastics
X transverse direction
Y longitudinal direction

The invention claimed is:

1. A disposable wearing article having a longitudinal direction, a transverse direction, and a thickness direction, the article comprising:
   a skin-facing side;
   a non-skin-facing side;
   a chassis including a front waist region, a rear waist region and a crotch region extending between the front and rear waist regions;
   a waist-opening defined by front and rear ends of the chassis;
   a pair of leg-openings defined by opposite lateral edges of the chassis;
   an absorbent structure lying at least in the crotch region;
   a pair of leg-cuffs lying on the skin-facing side of the chassis, extending across the crotch region into the front and rear waist regions and spaced apart from each other in the transverse direction;
   a plurality of front waist elastics extending in the transverse direction, spaced apart from each other in the longitudinal direction and contractibly attached under tension to the front waist region; and
   a plurality of rear waist elastics extending in the transverse direction, spaced apart from each other in the longitudinal direction and contractibly attached under tension to the rear waist region,
   wherein:
   the chassis includes an inner sheet lying on the skin-facing side, an outer sheet lying on the side opposite to the non-skin-facing side and the waist elastics attached between the inner and outer sheets,
   the absorbent structure extends across the crotch region into the front and rear waist regions,
   the absorbent structure includes a core material including at least one selected from the group consisting of fluff pulp and superabsorbent polymer particles,
   the absorbent structure is further formed with a core material lessened area extending in the longitudinal direction and having a lower thickness of the core material in comparison with an area surrounding the core material lessened area,
   the leg-cuffs respectively include
      lateral proximal portions bonded to the chassis,
      lateral distal portions opposed to the lateral proximal portions and adapted to be spaced upward from the chassis, and
      cuff elastics contractibly attached under tension to the lateral distal portions,
   at least one of (i) the plurality of front waist elastics and (ii) the plurality of rear waist elastics include
      first waist elastics lying on the chassis outboard of the absorbent structure as viewed in the longitudinal direction;
      second waist elastics lying inboard of the first waist elastics as viewed in the longitudinal direction, wherein middle segments of the second waist elastics in the transverse direction overlap the absorbent structure; and
      third waist elastics lying inboard of the second waist elastics as viewed in the longitudinal direction, wherein middle segments of the third waist elastics in the transverse direction overlap the absorbent structure,
   the core material lessened area of the absorbent structure overlaps at least the third waist elastics in the thickness direction,
   at least one of the front and rear waist regions includes
      a first sub-region provided with the first waist elastics,
      a third sub-region provided with the third waist elastics, and
      a second sub-region provided with the second waist elastics and lying between the first and third sub-regions,
   wherein a tensile stress in the first and third sub-regions is higher than that in the second sub-region and the cuff elastics extend at least to the second sub-region.

2. The disposable wearing article according to claim 1, wherein the respective lateral distal portions in the leg-cuffs are bonded to the skin-facing side of the chassis in regions overlapping the first sub-region.

3. The disposable wearing article according to claim 1, wherein a tensile stress in the first sub-region and the third sub-region is in a range of 0.5 to 3.0 N and a tensile stress in the second sub-region is in a range of 0.1 to 1.5 N.

4. The disposable wearing article according to claim 1, wherein a stiffness value in the first through third sub-regions inclusive of the absorbent structure is in a range of 0.05 to 1.00 N*cm.

5. The disposable wearing article according to claim 1, wherein a distance between adjacent first waist elastics in the longitudinal direction is greater than a distance between adjacent third waist elastics in the longitudinal direction.

6. The disposable wearing article according to claim 1, wherein the first, second and third waist elastics extend all the way in the transverse direction from one side edge of the corresponding front or rear waist region to the other transversely opposite side edge of the corresponding front or rear waist region.

\* \* \* \* \*